(12) United States Patent
Allouche et al.

(10) Patent No.: US 9,290,416 B1
(45) Date of Patent: Mar. 22, 2016

(54) METHOD FOR GEOPOLYMER CONCRETE

(71) Applicant: Louisiana Tech University Research Foundation, Ruston, LA (US)

(72) Inventors: Erez Nissim Allouche, Madison, MS (US); Eleazar Ivan Diaz-Loya, Parkville, MD (US)

(73) Assignee: Louisiana Tech Research Corporation, Ruston, LA (US)

( * ) Notice: Subject to any disclaimer, the term of this patent is extended or adjusted under 35 U.S.C. 154(b) by 0 days.

(21) Appl. No.: 14/819,080

(22) Filed: Aug. 5, 2015

Related U.S. Application Data (62) Division of application No. 13/481,494, filed on May 25, 2012.

(60) Provisional application No. 61/562,236, filed on Nov. 21, 2011.

(51) Int. Cl.
  *G05B 21/00* (2006.01)
  *C04B 7/26* (2006.01)

(52) U.S. Cl.
  CPC ........................................ *C04B 7/26* (2013.01)

(58) Field of Classification Search
  CPC .............................. C04B 12/005; G05B 21/00
  See application file for complete search history.

(56) References Cited

U.S. PATENT DOCUMENTS

| | | | |
|---|---|---|---|
| 3,609,316 A | 9/1971 | Brosset et al. | |
| 4,226,630 A | 10/1980 | Styron | |
| 5,527,387 A | 6/1996 | Andersen et al. | |
| 5,810,920 A | 9/1998 | Ueshima et al. | |
| 6,632,876 B2 | 10/2003 | Soukatchoff | |
| 7,347,896 B2 | 3/2008 | Harrison | |
| 7,386,368 B2 | 6/2008 | Andersen et al. | |
| 7,691,198 B2 | 4/2010 | Van Deventer et al. | |
| 8,337,612 B2 | 12/2012 | Abdullah et al. | |
| 8,512,468 B2 | 8/2013 | Allouche et al. | |

(Continued)

FOREIGN PATENT DOCUMENTS

WO 2011020975 2/2011

OTHER PUBLICATIONS

Diaz-Loya, E.I., "Development of Approximating Functions to Model and Predict the Properties of Fresh and Hardened Fly Ash-Based Geopolymer Concrete," PhD Dissertation, Louisiana Tech University, College of Engineering and Science (May 27, 2011).

(Continued)

*Primary Examiner* — Paul Marcantoni
(74) *Attorney, Agent, or Firm* — Jones Walker LLP (57) ABSTRACT

A geopolymer concrete prepared by predicting a mechanical property of a geopolymer concrete formed with each of a plurality of fly ash materials, selecting as a source material for the geopolymer concrete one of the fly ash materials that yields a predicted value of the mechanical property that is equal to or greater than a target value for the mechanical property, and mixing the fly ash source material with an alkaline activator solution, a fine aggregate, and a coarse aggregate. The prediction of the mechanical property includes measuring one or more properties of each of the plurality of fly ash materials, calculating predicted values of the mechanical property for geopolymer concretes formed with each of the plurality of fly ash materials using a predetermined equation relating the one or more properties of the plurality of fly ash materials to predicted values of the mechanical property of the geopolymer concrete.

7 Claims, 6 Drawing Sheets

(56) References Cited

U.S. PATENT DOCUMENTS

| | | |
|---|---|---|
| 8,562,735 B2 | 10/2013 | Allouche et al. |
| 8,873,033 B1 | 10/2014 | Allouche et al. |
| 2005/0016418 A1 | 1/2005 | Holbek |
| 2006/0287773 A1 | 12/2006 | Andersen et al. |
| 2008/0027583 A1 | 1/2008 | Andersen et al. |
| 2008/0027584 A1 | 1/2008 | Andersen et al. |
| 2008/0027685 A1 | 1/2008 | Andersen et al. |
| 2008/0066653 A1 | 3/2008 | Andersen et al. |
| 2011/0004332 A1 | 1/2011 | Andersen |
| 2011/0004333 A1 | 1/2011 | Andersen |
| 2012/0024196 A1 | 2/2012 | Gong et al. |
| 2012/0037043 A1 | 2/2012 | Zubrod |

OTHER PUBLICATIONS

Fernandez-Jimenez, A.M., Palomo, A., and Lopez-Hombrados, C., "Engineering properties of alkali-activited fly ash concrete," ACI Materials Journal, 103(2): 106-112 (2006).

Sofi, M., Van Deventer, J.S.J., Mendis, P.A., and Lukey, G.C., "Engineering properties of inorganic polymer concretes (IPCs)," Cement and Concrete Research, 37(2): 251-257 (2007).

Yunsheng, Z., Wei, S., Qianli, C., and Lin,C., Synthesis and heavy metal immobilization behaviors of slag based geopolymer, Journal of Hazardous Materials 143, 206-213 (2007).

PCT International Searching Authority/US, International Search Report, mailed Apr. 20, 2012, for PCT/US2011/65854, "Geopolymer Mortar and Method" (related to co-pending application).

PCT International Searching Authority/US, Written Opinion of the International Searching Authority, mailed Apr. 20, 2012, for PCT/US2011/65854, "Geopolymer Mortar and Method" (related to co-pending application).

Co-pending U.S. Appl. No. 13/481,494, "Method for Geopolymer Concrete," Erez Nissim Allouche and Eleazar Ivan Diaz-Loya, filed May 25, 2012.

Co-pending U.S. Appl. No. 14/469,687, "Geopolymer with Nanoparticle Retardant and Method," Erez Allouche, Yuri Lvov, Carlos Montes, and Anupam Joshi, filed Aug. 27, 2014.

Co-pending U.S. Appl. No. 14/496,449, "Cured-In-Place-Pipe Liner Inspection System and Method," Erez Allouche and Shaurav Alam, filed Sep. 25, 2014.

METHOD FOR GEOPOLYMER CONCRETE

CROSS-REFERENCE TO RELATED PATENT APPLICATION

This application is a division of and claims priority to U.S. patent application Ser. No. 13/481,494, filed on May 25, 2012, which claims priority to U.S. Provisional Application No. 61/562,236, filed on Nov. 21, 2011, both of which are incorporated herein by reference.

SUMMARY OF SELECTED EMBODIMENTS OF INVENTION

A geopolymer concrete prepared by the process including the following steps: (a) determining a target value for a mechanical property of the geopolymer concrete; (b) predicting the mechanical property of a geopolymer concrete formed with each of a plurality of fly ash materials; (c) selecting one of the plurality of fly ash materials as a fly ash source material for the geopolymer concrete, where the selected fly ash material yields a predicted value of the mechanical property that is equal to or greater than the target value for the mechanical property; and (d) mixing of components. Alternatively, the fly ash material yielding the greatest predicted value of the mechanical property may be selected as a fly ash source material for the geopolymer concrete, without regard to the target value of the mechanical property or without first determining a target value for the mechanical property of the geopolymer concrete. The components mixed may include about 14 to about 24% by volume fly ash source material, about 25 to about 40% by volume fine aggregate, about 32 to about 41% by volume coarse aggregate, about 1 to about 20% by volume alkaline activator solution. In one alternative, about 1% by volume superplasticizer may be added to the mixture. The prediction of the mechanical property of a geopolymer concrete formed with each of the plurality of fly ash materials may include (1) measuring one or more properties of each of the plurality of fly ash materials; (2) calculating predicted values of the mechanical properties for geopolymer concretes formed with each of the plurality of fly ash materials using a predetermined equation relating the one or more properties of the plurality of fly ash materials to predicted values of the mechanical property of the geopolymer concrete; and (3) comparing the predicted values of the mechanical property with the target value for the mechanical property. The mechanical property may be compressive strength. The one or more properties of the plurality of fly ash materials may be silica concentration, alumina concentration, calcium oxide concentration, and mean particle size. The predetermined equation may be:

$$f_C = 16.22 + 1.33*SiO_2 - 0.78*Al_2O_3 + 0.71*CaO - 0.90*d50,$$

where $f_C$ is the compressive strength of the geopolymer concrete in MPa, $SiO_2$ is the silica concentration in weight percent, $Al_2O_3$ is the alumina concentration in weight percent, CaO is the calcium oxide concentration in weight percent, and d50 is the mean particle size in μm.

Alternatively, the one or more properties of the plurality of fly ash materials may be reactive silica concentration, reactive alumina concentration, reactive calcium oxide concentration, mean particle size, and loss on ignition. The predetermined equation may be:

$$f_C = -3.62 + 0.59*RSiO_2 + 3.35*RAl_2O_3 - 0.48*RCaO - 0.74*d50 - 4.39*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in μm, and LOI is the percent loss on ignition. In another alternative, the predetermined equation may be:

$$f_C = -3.68 + 0.59*RSiO_2 + 3.35*RAl_2O_3 - 0.49*RCaO - 0.74*d50 - 4.40*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in μm, and LOI is the percent loss on ignition. In yet another alternative, the predetermined equation may be:

$$f_C = 9.51 + 0.52*RSiO_2 + 2.16*RAl_2O_3 - 0.066*RCaO - 0.69*d50 - 1.70*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in μm, and LOI is the percent loss on ignition.

A method of selecting a fly ash source material for a geopolymer concrete from a plurality of fly ash materials may include the following steps: (a) determining a target value for a mechanical property of the geopolymer concrete; (b) measuring one or more properties of each of the plurality of fly ash materials; (c) calculating predicted values of the mechanical property for geopolymer concretes formed with each of the plurality of fly ash materials using a predetermined equation relating the one or more properties of the plurality of fly ash materials to predicted values of the mechanical property of the geopolymer concrete; (d) comparing the predicted values of the mechanical property with the target value for the mechanical property; (e) selecting one of the plurality of fly ash materials as the fly ash source material for the geopolymer concrete, where the selected fly ash material yields a predicted value of the mechanical property that is equal to or greater than the target value for the mechanical property; and (f) preparing the geopolymer concrete with the fly ash source material. The mechanical property may be compressive strength. The one or more properties of the plurality of fly ash materials may be silica concentration, alumina concentration, calcium oxide concentration, and mean particle size. The predetermined equation may be:

$$f_C = 16.22 + 1.33*SiO_2 - 0.78*Al_2O_3 + 0.71*CaO - 0.90*d50,$$

where $f_C$ is the compressive strength of the geopolymer concrete in MPa, $SiO_2$ is the silica concentration in weight percent, $Al_2O_3$ is the alumina concentration in weight percent, CaO is the calcium oxide concentration in weight percent, and d50 is the mean particle size in μm.

Alternatively, the one or more properties of the plurality of fly ash materials may be reactive silica concentration, reactive alumina concentration, reactive calcium oxide concentration, mean particle size, and loss on ignition. The predetermined equation may be:

$$f_C = -3.62 + 0.59*RSiO_2 + 3.35*RAl_2O_3 - 0.48*RCaO - 0.74*d50 - 4.39*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in μm, and LOI is the percent loss on ignition. In another alternative, the predetermined equation may be:

$$f_C = -3.68 + 0.59*RSiO_2 + 3.35*RAl_2O_3 - 0.49*RCaO - 0.74*d50 - 4.40*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in μm, and LOI is the percent loss on ignition. In yet another alternative, the predetermined equation may be:

$$f_C = 9.51 + 0.52*RSiO_2 + 2.16*RAl_2O_3 - 0.066*RCaO - 0.69*d50 - 1.70*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in μm, and LOI is the percent loss on ignition.

A method of selecting a fly ash source material for a geopolymer concrete from a plurality of fly ash materials includes the following steps: (a) determining a target value for a mechanical property of the geopolymer concrete; (b) measuring one or more properties of a first fly ash material, where the first fly ash material is one of the plurality of fly ash materials; (c) calculating a first predicted value of the mechanical property for a first geopolymer concrete formed with the first fly ash material using a predetermined equation relating the one or more properties of the plurality of fly ash materials to predicted values of the mechanical property of the geopolymer concrete; (d) comparing the first predicted value of the mechanical property with the target value for the mechanical property; (e) selecting the first fly ash material as the fly ash source material for the geopolymer concrete if the first predicted value of the mechanical property is equal to or greater than the target value for the mechanical property. If the first predicted value of the mechanical property is less than the target value for the mechanical property, the method may further include the following steps: (f) measuring one or more properties of a second fly ash material, where the second fly ash material is one of the plurality of fly ash materials; (g) calculating a second predicted value of the mechanical property for a second geopolymer concrete formed with the second fly ash material using the predetermined equation; (h) comparing the second predicted value of the mechanical property with the target value for the mechanical property; (i) selecting the second fly ash material as the fly ash source material for the geopolymer concrete if the second predicted value of the mechanical property is equal to or greater than the target value for the mechanical property. If the second predicted value of the mechanical property is less than the target value for the mechanical property, the method may further include repeating steps (f) through (i) for each of the remaining plurality of fly ash materials until a fly ash source material is selected.

A method of preparing a geopolymer concrete from a fly ash source material may include the following steps: (a) determining a target value for a mechanical property of the geopolymer concrete; (b) predicting the mechanical property of the geopolymer concrete prepared with the fly ash source material; (c) changing one or more properties of the fly ash source material to adjust the predicted mechanical property of the geopolymer concrete towards to the target value; and (d) preparing the geopolymer concrete with the fly ash source material.

A method of predicting a mechanical property of a geopolymer concrete formed from a fly ash material may include the following steps: (a) measuring one or more properties of the fly ash material; (b) calculating a predicted value of the mechanical property of the geopolymer concrete using a predetermined equation relating the one or more properties of the fly ash material to the mechanical property of the geopolymer concrete. The mechanical property may be compressive strength. The one or more properties of the fly ash material may be silica concentration, alumina concentration, calcium oxide concentration, and mean particle size. The predetermined equation may be:

$$f_C = 16.22 + 1.33*SiO_2 - 0.78*Al_2O_3 + 0.71*CaO - 0.90*d50,$$

where $f_C$ is the compressive strength of the geopolymer concrete in MPa, $SiO_2$ is the silica concentration in weight percent, $Al_2O_3$ is the alumina concentration in weight percent, CaO is the calcium oxide concentration in weight percent, and d50 is the mean particle size in μm.

Alternatively, the one or more properties of the fly ash material may be reactive silica concentration, reactive alumina concentration, reactive calcium oxide concentration, mean particle size, and loss on ignition. The measuring in step (a) may further include: (1) measuring a silica concentration, an alumina concentration, and a calcium oxide concentration in the fly ash material; (2) measuring the concentration of each silica-containing crystalline phase, each alumina-containing crystalline phase, and each calcium-oxide-containing crystalline phase in the fly ash material; (3) identifying the concentration of silica in the silica-containing crystalline phases, the concentration of alumina in the alumina-containing crystalline phases, and the concentration of calcium oxide in the calcium-oxide-containing crystalline phases; (4) calculating the concentration of non-reactive silica in the fly ash material by totaling the products of the concentration of silica in each silica-containing crystalline phase and the concentration of that silica-containing crystalline phase in the fly ash material; (5) calculating the concentration of non-reactive alumina in the fly ash material by totaling the products of the concentration of alumina in each alumina-containing crystalline phase and the concentration of that alumina-containing crystalline phase in the fly ash material; (6) calculating the concentration of non-reactive calcium oxide in the fly ash material by totaling the products of the concentration of calcium oxide in each calcium-oxide-containing crystalline phase and the concentration of that calcium-oxide-containing crystalline phase in the fly ash material; (7) subtracting the concentration of non-reactive silica in the fly ash material from the silica concentration; (8) subtracting the concentration of non-reactive alumina in the fly ash material from the alumina concentration; and (9) subtracting the concentration of non-reactive calcium oxide in the fly ash material from the calcium oxide concentration.

In this alternative, the predetermined equation may be:

$$f_C = -3.62 + 0.59*RSiO_2 + 3.35*RAl_2O_3 - 0.48*RCaO - 0.74*d50 - 4.39*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in µm, and LOI is the percent loss on ignition. In another alternative, the equation may be:

$$f_C = -3.68 + 0.59*RSiO_2 + 3.35*RAl_2O_3 - 0.49*RCaO - 0.74*d50 - 4.40*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in µm, and LOI is the percent loss on ignition. In yet another alternative, the equation may be:

$$f_C = 9.51 + 0.52*RSiO_2 + 2.16*RAl_2O_3 - 0.066*RCaO - 0.69*d50 - 1.70*LOI,$$

where $f_C$ is the compressive strength of the geopolymer concrete in MPa, $RSiO_2$ is the reactive silica concentration in weight percent, $RAl_2O_3$ is the reactive alumina concentration in weight percent, RCaO is the reactive calcium oxide concentration in weight percent, d50 is the mean particle size in µm, and LOI is the percent loss on ignition.

The method of predicting a mechanical property of a geopolymer concrete formed from a fly ash material may include the following additional step: (c) calculating a predicted value of a second mechanical property for the geopolymer concrete using a second predetermined equation relating the predicted values of the mechanical property to the predicted values of the second mechanical property. The mechanical property may be compressive strength, and the second mechanical property may be flexural strength. The second predetermined equation may be:

$$f_r = 0.69\sqrt{f_C},$$

where $f_r$ is the flexural strength of the geopolymer concrete in MPa and $f_C$ is the compressive strength of the geopolymer concrete in MPa. Alternatively, the second mechanical property may be static elastic modulus. The second predetermined equation may be:

$$E_C = 580 f_C,$$

where $E_C$ is the static elastic modulus in MPa and $f_C$ is the compressive strength of the geopolymer concrete in MPa. Alternatively, the second predetermined equation may be:

$$E_C = 0.037(w)^{1.5}\sqrt{f_C},$$

where $E_C$ is the static elastic modulus in MPa, w is the density of the geopolymer concrete in $kg/m^3$, and $f_C$ is the compressive strength of the geopolymer concrete in MPa.

DETAILED DESCRIPTION OF THE SELECTED EMBODIMENTS

According to a recent survey released by the American Coal Ash Association (ACAA), the United States produced approximately 136 million tons of coal combustion products in 2008 making it the second largest by-product stream in the United States. The combustion of finely ground coal to produce electricity typically leaves behind two main waste streams: (1) bottom ash, composed of particles of sizes ranging from 63-1000 µm many times fused together that drop to the bottom of the boiler; and (2) fly ash, which is transported along with the flue gases and captured by pollution control devices.

Fly ash is a very fine and powdery material composed mainly of spherically shaped particles that range in size from a few microns to over 100 µm. The chemical composition of fly ash is very similar to that of volcanic ash having as main components: silica, alumina, iron oxide, and calcium oxide in some cases. Typically, a small portion of the chemical components of fly ash is arranged in a crystalline pattern (e.g., quartz, mullite, lime, magnetite) with the rest held in amorphous states with no particular arrangement due to the rapid cooling of fly ash after leaving the boiler.

Fly ash is also a pozzolan. In other words, fly ash is a material that reacts with calcium hydroxide in the presence of water to create cementitious compounds. Fly ash has been used in ordinary Portland cement (OPC) as a supplementary cementitious material in order to improve its rheology in the fresh mix and durability of the hardened product. Fly ash alone, however, is capable of producing a strong cementitious binder when activated under highly alkaline conditions. This binder is referred to as a geopolymer, and it does not require the presence of OPC to harden or gain strength. The alkaline condition is usually provided by a sodium hydroxide solution or a potassium hydroxide solution and an alkaline silicate, such as sodium silicate or potassium silicate. Because freshly mixed geopolymer concrete is more viscous than ordinary concrete, use of a water reducer or superplasticizer is recommended to improve workability of the freshly mixed geopolymer concrete. Geopolymers are typically cured under slightly elevated temperatures up to 60° C. Heat acts as a catalyst accelerating the formation of the geopolymer binder, and increasing the strength of the resulting geopolymer concrete. Geopolymer concrete possesses mechanical strength that is similar to or even greater than that of ordinary concrete. Geopolymers are particularly resilient in thermal related applications. Geopolymers are practically inert to sulfate-induced corrosion, as the strength of geopolymers is not based on calcium aluminates, which are susceptible to sulfate attack. Use of geopolymers is ecofriendly in that it reduces the need for OPC and associated carbon dioxide emissions. Use of geopolymers also converts coal combustion products into beneficial construction materials, which reduces landfill and disposal facility requirements.

Geopolymerization is the process by which geopolymers harden by forming polymeric chains due to the polycondensation of ortho-sialate ions. Geopolymerization occurs when fly ash is mixed with an alkaline activator solution. The geopolymerization reaction is believed to include three steps: (1) dissolution of silicon and aluminum species from the source material through the action of the alkaline activator solution, (2) transportation of species and formation of monomers, and (3) polycondensation and growth of polymeric structures resulting in the hardening of the material.

Many researchers agree that parallel to the formation of the geopolymer gel, calcium in the mixture reacts with silicate and aluminate monomers dissolved in the source material, forming calcium silicate hydrates (CSH) and calcium aluminosilicate hydrates (CASH). The hydration of these compounds leads to water deficiency and thus raises the alkalinity of the mixture. The higher alkalinity promotes higher and faster dissolution of silicate and aluminate species from the source material, which increases the rate of geopolymerization. Thus, the presence of calcium in the fly ash source material contributes to mechanical strength of the resulting hardened matrix not only by forming CSH and CASH, but also by enhancing the geopolymerization process.

Geopolymer research usually uses highly pure sources of silica and alumina, such as metakaolin. Fly ash, however, has significantly different particle morphology and contains impurities that fluctuate depending upon the fly ash source, which impacts the mechanical properties of the resulting geopolymer concretes. Geopolymer binders used in dry cast applications have been found to result in geopolymers having highly variable mechanical properties depending upon the raw material used, such as metakaolin or fly ash. The chemical properties of fly ash depend upon the type and composition of its precursor coal, leading to significant variability of fly ash from different sources.

Other factors play a significant role in the mechanical properties of a geopolymer formed with fly ash. Impurities, such as calcium oxide, positively impact the geopolymer, but cause shorter setting times due to the creation of nucleation sites. The crystallographic properties of fly ash affect the resulting geopolymer. Amorphous compounds dissolve easier than crystalline compounds during the first step of geopolymerization, and yield higher amounts of reactive silica and alumina to combine during the second step of geopolymerization, resulting in a higher degree of geopolymerization and higher mechanical strength. Because a significant part of the geopolymerization reaction occurs at the particle-liquid interface, finer fly ash particles result in greater surface area rendering the fly ash more reactive. Also, poor burning efficiency yields unburned coal in the fly ash. The amount of unburned coal in fly ash is quantified as loss on ignition (LOI). Fly ash containing a large amount of unburned carbon with high surface area could adversely impact the behavior of the fresh mixture by creating a demand for the addition of activator solution well beyond that needed to activate the source material to obtain a workable mixture.

A set of statistically derived equations were developed to assist in the preparation of fly ash based geopolymer concretes having predictable mechanical properties. The input values of the equations are chemical, crystallographic, and physical characteristics of fly ash materials, and the output values of the equations are mechanical properties of the geopolymer concrete.

Thirty-four fly ash samples were analyzed. Each fly ash sample was used as a source material for a geopolymer concrete, and the resulting geopolymer concretes were analyzed. Twenty-four samples were used for data analysis and model building, while the remaining samples were used for validation purposes. Fourteen fly ash samples were type C fly ash, and twenty fly ash samples were type F fly ash according to ASTM specification C 618. These fly ash samples were collected from different coal-fired power generating stations around the United States.

Chemical, X-ray diffraction (XRD), scanning electron microscopy (SEM), and particle size distribution analyses were performed for each fly ash sample. Geopolymer paste samples were analyzed using XRD and Raman spectroscopy. For each geopolymer concrete product, measurements were made of the setting time, compressive strength, flexural strength, static elastic modulus, and Poisson's ratio. Correlations were identified between the fly ash's chemical and crystallographic characteristics and the geopolymer concrete's mechanical properties. Correlations were also made among the mechanical properties of geopolymer concrete.

The mix design for the geopolymer concrete specimens is presented in Table 1. It was established using the absolute volume method proposed by the Portland Cement Association in 2009. The quantities in Table 1 are estimates; small adjustments were made to the activator solution to fly ash ratio depending on the liquid demand of each fly ash source material to obtain a slump of 10 to 15 cm. In other words, the amount of fly ash, fine aggregate, and coarse aggregate in the mixture varied slightly as more or less activator solution was added to obtain the desired slump value.

TABLE 1

| Material | Quantity (kg/m$^3$) |
| --- | --- |
| Fly Ash | 494 |
| Fine Aggregate | 691 |
| Coarse Aggregate | 858 |
| Activator Solution | 198-464 |
| Superplasticizer | 15 |

The alkaline activator solution used was composed of a 14 M sodium hydroxide solution and sodium silicate type "D" from PQ Corporation, which was 45% by weight sodium silicate and had a $SiO_2$ to $Na_2O$ ratio of 2:1. Tap water was used throughout the experiments in an attempt to mimic field conditions. The two solutions were mixed in a 1:1 ratio by weight. Well graded sand with a bulk density of 1680 kg/m$^3$ (100 lb/ft$^3$), a specific gravity of 2.63, and a fineness modulus of 2.4 served as the fine aggregate. "Pea gravel" (1 cm or ⅜ in. diameter) with a bulk density of 1934 kg/m$^3$ (115 lb/ft$^3$) and specific gravity of 2.70 acted as the coarse aggregate. In order to improve the workability of the fresh geopolymer concrete, the superplasticizer Glenium 7101® (manufactured by BASF) was incorporated 60 s before the end of the mixing cycle.

The ingredients were mixed in a vertical mixer with planetary action (i.e., the beater rotates on its axis in opposite directions as it moves around the bowl). In order to promote the first phase of geopolymerization, dissolution of silicate and aluminate species, the following mixing procedure was followed: (1) fly ash and sodium hydroxide solution were mixed for 30 s; (2) sodium silicate was added and mixed for 30 s; (3) sand was added and mixed for 60 s; and (4) gravel was added and mixed for an additional 120 s with the superplasticizer added 60 s before the end of the mixing cycle. For fly ash samples that formed geopolymer concretes with extremely short setting times, the mixing times were shortened enough to cast and form the species.

Each sample was poured into a 75×150 mm cylinder and the compressive strength of each sample was determined following ASTM standard C-39. Setting time measurements of fresh geopolymer paste samples were taken using a standard Vicat needle. All samples were stripped from the mold after 24 hours, cured for three days at 60° C., taken out of the oven, and allowed to cool at room temperature for 24 hours prior to testing.

Table 2 displays the chemical characteristics in weight percentage of fly ash samples obtained from the chemical analysis performed via X-ray fluorescence (XRF) following ASTM standard D-4326. Higher LOI values resulted in more hygroscopic mixtures, thus requiring additional alkaline activator solution to obtain the desired consistency, which may have led to lower compressive strength in the geopolymer concrete samples.

TABLE 2

| Class | Sample | $SiO_2$ | $Al_2O_3$ | $SiO_2/Al_2O_3$ | $SiO_2+Al_2O_3$ | CaO | $Fe_2O_3$ | LOI |
|---|---|---|---|---|---|---|---|---|
| C | 1 | 37.77 | 19.13 | 1.97 | 56.90 | 22.45 | 7.33 | 0.17 |
| C | 2 | 32.41 | 18.40 | 1.76 | 57.90 | 28.07 | 7.17 | 0.38 |
| C | 3 | 55.61 | 19.87 | 2.80 | 75.48 | 12.93 | 4.52 | 0.23 |
| F | 4 | 58.52 | 20.61 | 2.84 | 79.13 | 5.00 | 9.43 | 0.05 |
| F | 5 | 61.01 | 20.06 | 3.04 | 81.07 | 5.48 | 7.00 | 0.08 |
| F | 6 | 61.23 | 19.20 | 3.19 | 80.43 | 5.64 | 7.27 | 0.06 |
| F | 7 | 62.12 | 19.59 | 3.17 | 81.71 | 5.01 | 6.88 | 0.10 |
| F | 8 | 59.32 | 19.72 | 3.01 | 79.04 | 6.90 | 7.22 | 0.15 |
| C | 9 | 48.70 | 16.60 | 2.93 | 65.30 | 18.72 | 6.93 | 0.49 |
| F | 10 | 55.07 | 28.61 | 1.92 | 83.68 | 1.97 | 6.22 | 1.82 |
| F | 11 | 56.22 | 27.15 | 2.07 | 83.37 | 5.43 | 3.73 | 2.69 |
| F | 12 | 56.39 | 27.36 | 2.06 | 83.75 | 4.69 | 3.34 | 3.41 |
| F | 13 | 57.11 | 28.18 | 2.03 | 85.29 | 5.18 | 4.00 | 0.44 |
| F | 14 | 57.35 | 27.78 | 2.06 | 85.13 | 5.57 | 3.65 | 0.83 |
| F | 15 | 40.75 | 22.79 | 1.79 | 63.54 | 4.64 | 17.76 | 5.72 |
| F | 16 | 66.50 | 18.80 | 3.54 | 85.30 | 4.91 | 1.95 | 0.26 |
| C | 17 | 39.25 | 21.09 | 1.86 | 60.34 | 23.53 | 4.99 | 0.11 |
| C | 18 | 33.02 | 19.82 | 1.67 | 52.84 | 26.19 | 6.75 | 0.16 |
| F | 19 | 59.25 | 18.43 | 3.21 | 77.68 | 9.23 | 5.61 | 0.04 |
| C | 20 | 56.42 | 17.63 | 3.20 | 74.05 | 11.66 | 5.74 | 0.00 |
| C | 21 | 27.15 | 17.57 | 1.55 | 44.72 | 33.39 | 6.08 | 0.00 |
| C | 22 | 31.26 | 19.76 | 1.58 | 51.02 | 28.53 | 6.47 | 0.00 |
| C | 23 | 30.85 | 17.07 | 1.81 | 47.92 | 28.47 | 6.79 | 0.00 |
| C | 24 | 49.90 | 19.32 | 2.58 | 69.22 | 15.22 | 7.63 | 0.09 |
| C | 25 | 55.15 | 23.55 | 2.34 | 78.70 | 10.60 | 4.63 | 0.31 |
| F | 26 | 52.81 | 20.83 | 2.54 | 73.64 | 0.98 | 13.05 | 0.19 |
| F | 27 | 45.65 | 20.37 | 2.24 | 66.02 | 6.23 | 19.43 | 0.20 |
| F | 28 | 58.04 | 28.15 | 2.06 | 86.19 | 4.24 | 3.29 | 0.07 |
| F | 29 | 51.46 | 28.04 | 1.84 | 79.50 | 2.96 | 10.34 | 0.03 |
| F | 30 | 51.69 | 21.37 | 2.42 | 73.06 | 3.10 | 8.28 | 0.22 |
| C | 31 | 57.55 | 19.84 | 2.90 | 77.39 | 10.25 | 5.08 | 0.07 |
| F | 32 | 52.57 | 25.22 | 2.08 | 77.79 | 5.10 | 7.76 | 0.13 |
| F | 33 | 36.18 | 17.70 | 2.04 | 53.88 | 2.26 | 10.59 | 27.84 |
| C | 34 | 33.38 | 14.72 | 2.27 | 48.10 | 26.80 | 7.69 | 2.83 |
| F | MIN | 36.18 | 17.70 | 1.79 | 53.88 | 0.98 | 1.95 | 0.03 |
|  | MAX | 66.50 | 28.61 | 3.54 | 86.19 | 9.23 | 19.43 | 27.84 |
|  | AVG | 54.96 | 23.00 | 2.46 | 77.96 | 4.73 | 7.84 | 2.22 |
| C | MIN | 27.15 | 14.72 | 1.55 | 44.72 | 10.25 | 4.52 | 0.00 |
|  | MAX | 57.55 | 23.55 | 3.20 | 78.70 | 33.39 | 7.69 | 2.83 |
|  | AVG | 42.03 | 18.88 | 2.23 | 61.42 | 21.20 | 6.27 | 0.35 |

Figure 1:
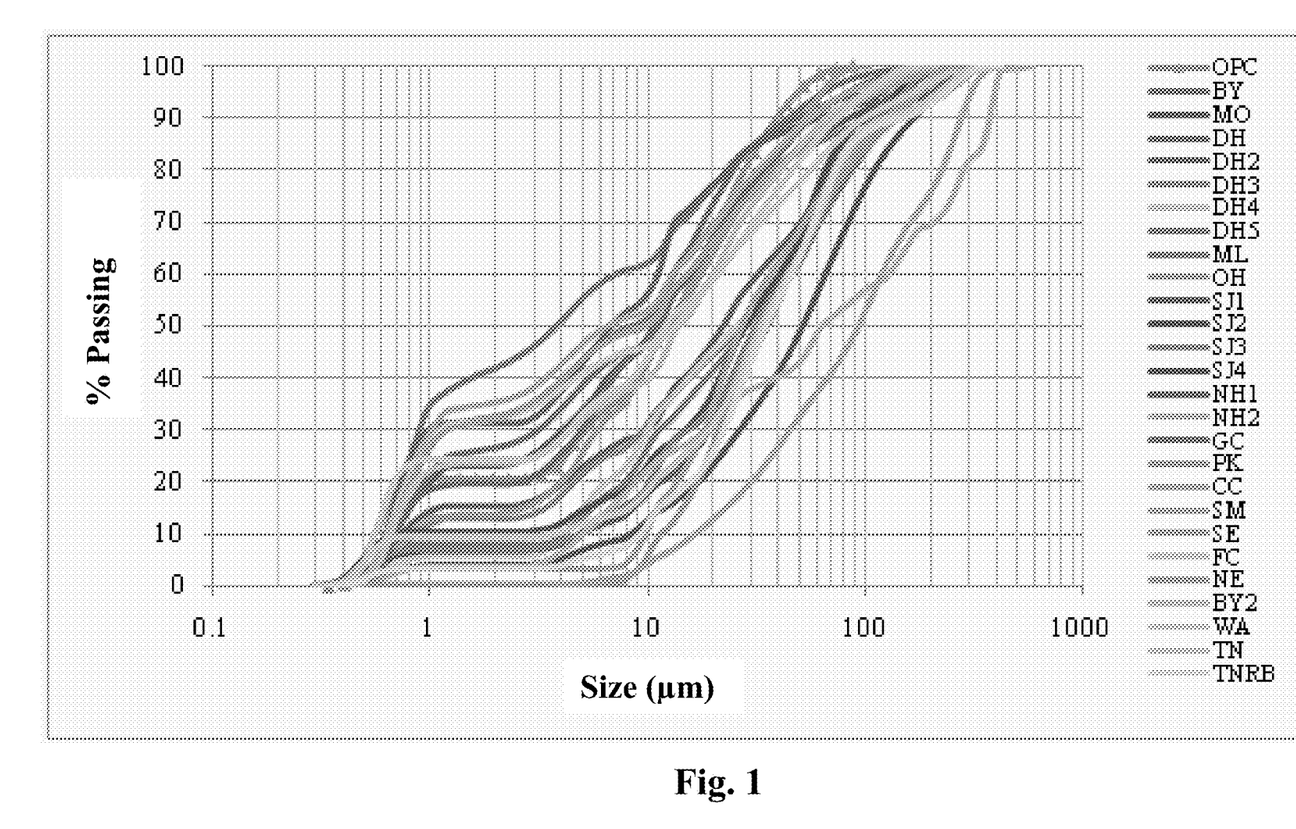
FIG. 1 is a graphical representation of the particle size distribution of selected fly ash source material samples.

Analysis of the particle size distribution was conducted for each fly ash sample using Microtrac S3500 laser-based equipment with a measuring range between 0.024 μm and 2816 μm. Samples were suspended in isopropyl alcohol and went through the necessary cycles of reading and dispersing using ultrasound to obtain a realistic analysis. FIG. 1 shows the particle size distribution curves of selected fly ash samples. Also, Table 3 shows a summary of the physical properties of the fly ash samples including specific surface area and mean particle size. Particle size distribution is among the most important physical properties impacting the reactivity of fly ash material. The geopolymerization reaction occurs mostly at the surface of the fly ash particles. Smaller particles result in greater surface area, which leads to higher reactivity in the fly ash and higher compressive strength in the geopolymer concrete. Particle size also affects the packing characteristics and workability of fresh geopolymer concrete, as well as water demand. Particle size further affects the mechanical properties of the hardened geopolymer concrete.

TABLE 3

| Sample | Particles <45 μm (%) | Calculated surface $m^2/cm^3$ | Mean particle size (μm) | Specific gravity | Specific surface area ($m^2/g$) |
|---|---|---|---|---|---|
| 1 | 830.1 | 2.92 | 11.36 | 2.50 | 1.17 |
| 2 | 83.80 | 2.58 | 12.31 | 2.53 | 1.02 |
| 3 | 68.75 | 1.33 | 20.87 | 2.38 | 0.56 |
| 4 | 63.50 | 0.57 | 27.52 | 2.32 | 0.25 |
| 5 | 66.17 | 1.25 | 22.68 | 2.27 | 0.55 |
| 6 | 63.75 | 1.10 | 24.93 | 2.29 | 0.48 |
| 7 | 61.66 | 0.98 | 28.31 | 2.27 | 0.43 |
| 8 | 62.97 | 1.12 | 29.96 | 2.23 | 0.50 |
| 9 | 74.24 | 2.00 | 15.17 | 2.47 | 0.81 |
| 10 | 71.26 | 1.08 | 22.30 | 2.17 | 0.50 |
| 11 | 55.39 | 0.49 | 40.03 | 1.78 | 0.28 |
| 12 | 58.19 | 0.795 | 34.57 | 1.73 | 0.46 |
| 13 | 58.02 | 0.59 | 36.73 | 1.82 | 0.32 |
| 14 | 43.31 | 0.23 | 51.11 | 1.81 | 0.13 |
| 15 | 87.50 | 2.95 | 6.62 | 2.52 | 1.17 |
| 16 | 30.28 | 0.14 | 92.41 | 1.47 | 0.10 |
| 17 | 84.27 | 2.45 | 11.88 | 2.51 | 0.98 |
| 18 | 85.68 | 2.49 | 11.32 | 2.7 | 0.92 |
| 19 | 63.24 | 1.18 | 30.38 | 2.18 | 0.54 |
| 20 | 67.33 | 0.57 | 25.93 | 2.27 | 0.25 |
| 21 | 80.91 | 3.13 | 10.38 | 2.67 | 1.17 |
| 22 | 85.56 | 3.14 | 6.71 | 2.55 | 1.23 |
| 23 | 81.23 | 2.79 | 12.16 | 2.61 | 1.07 |
| 24 | 84.23 | 1.58 | 11.95 | 2.41 | 0.66 |
| 25 | 63.10 | 1.40 | 30.15 | 2.05 | 0.68 |
| 26 | 60.20 | 0.53 | 33.31 | 2.03 | 0.26 |
| 27 | 76.06 | 0.55 | 21.00 | 2.50 | 0.22 |
| 28 | 76.15 | 1.07 | 20.42 | 1.88 | 0.57 |
| 29 | 73.11 | 1.58 | 20.39 | 2.19 | 0.72 |
| 30 | 60.02 | 1.12 | 32.64 | 2.04 | 0.55 |
| 31 | 65.18 | 1.06 | 25.38 | 2.11 | 0.50 |
| 32 | 75.22 | 1.80 | 18.41 | 2.263 | 0.79 |

Figure 2A:
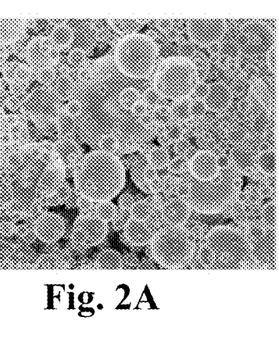
FIG. 2A is a scanning electron microscopy image of a fly ash source material before geopolymerization.
Figure 2B:
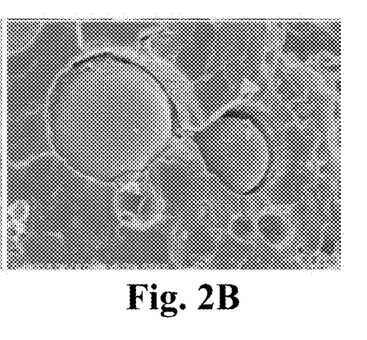
FIG. 2B is a scanning electron microscopy image of a geopolymerized fly ash source material sample.

SEM micrographs of each fly ash sample were taken before and after geopolymerization using a Hitachi S-4800 scanning electron microscope. FIG. 2A shows an SEM image of a fly ash sample before geopolymerization. This image shows the spherical nature of fly ash particles. FIG. 2B shows an SEM image of a fly ash sample after geopolymerization. This image shows the geopolymer gel surrounding unreacted larger fly ash particles.

Geopolymer paste samples were also analyzed using Raman spectroscopy. Spectra from 200 to 2700 $cm^{-1}$ were collected on an R-3000-HR Raman spectrometer from Raman Systems using a 785 nm diode laser operating at 290 mW through a fiber optic probe.

Tables 4-10 show the XRD quantitative analysis results of the fly ash samples and the corresponding geopolymer paste samples. XRD data was obtained using a Bragg-Brentano geometry powder diffractometer using a copper anode at 40 kV. Data was collected between 10° and 65° of two theta angles, with a step size of 0.05° and a count time of 5 s per step. Samples were further analyzed using the Rietveld phase quantification method to determine the amount of crystalline and amorphous components. XRD analysis of cementitious materials provides phase, chemical, and crystal structure information. Diffraction patterns of each phase are unique, and in a mixture their intensities are proportional to phase concentration.

TABLE 4

| Phase | 1 FA | 1 GP | 2 FA | 2 GP | 3 FA | 3 GP | 4 FA | 4 GP | 5 FA | 5 GP |
|---|---|---|---|---|---|---|---|---|---|---|
| Albite | | | | | 0.10 | | | | | |
| Allophane | | | | | | | | 9.30 | | |
| Anhydrite | | | 1.70 | | | | | | | |
| Calcium Catena Silicate | | | 0.40 | 0.30 | | | | | | |
| Dicalcium Silicate Silicate | | | 3.30 | 3.00 | | | | | | |
| Diopside | | | | 1.50 | | | | | | |
| Dolomite | | | | | 0.40 | | | | | |
| Gehlenite | | | | 0.60 | | | | | | |
| Grossular | | | 1.20 | 0.60 | | | | | | |
| Hematite | 0.30 | 0.30 | | | 0.30 | | 1.30 | 1.30 | 1.90 | 1.90 |
| Lime | 0.30 | 0.10 | | | | | | | | |
| Magnetite | 0.40 | 0.10 | 0.90 | | 0.60 | | | | 0.50 | 1.40 |
| Merwinite | 9.60 | 5.80 | | | | | | | | |
| Mullite | | | 1.40 | 0.20 | 1.30 | 2.10 | 6.70 | 7.30 | 10.60 | 5.80 |
| Nosean | | | | 2.20 | | | | | | |
| Periclase | 3.20 | 0.20 | 1.80 | 1.10 | 0.40 | 0.50 | | | | |
| Perovskite | | | 7.90 | 3.60 | | | 2.10 | 2.00 | | |
| Pseudobrookite | 4.20 | 1.40 | | | | | | | | |
| Quartz | 23.10 | 18.30 | 5.10 | 2.50 | 28.30 | 17.30 | 37.00 | 24.80 | 14.90 | 17.00 |
| Amorphous | 58.90 | 73.80 | 76.20 | 84.40 | 69.30 | 80.10 | 52.90 | 55.30 | 72.10 | 73.90 |

TABLE 5

| Phase | 6 FA | 6 GP | 7 FA | 7 GP | 8 FA | 8 GP | 9 FA | 9 GP | 10 FA | 10 GP |
|---|---|---|---|---|---|---|---|---|---|---|
| Calcite | | | | | | | 1.60 | 2.70 | | |
| Dolomite | | | | | | | 0.20 | 0.30 | | |
| Gypsum | | | | | | | 1.30 | | | |
| Hematite | 0.20 | | | | | 0.20 | | | | |
| Magnesite | | | | | | | 0.90 | 1.50 | | |
| Magnetite | 0.20 | 0.10 | 0.90 | 0.60 | 1.00 | 0.80 | | | | |
| Mullite | 5.30 | 2.90 | 6.20 | 3.70 | 5.20 | 4.80 | | | 25.27 | 14.62 |
| Periclase | | | | | | | 0.10 | 0.10 | | |
| Pyrite | | | | | | | 0.65 | 0.20 | | |
| Thermonatrite | | | | 9.30 | | | | | | |
| Quartz | 19.20 | 10.20 | 22.30 | 9.90 | 20.70 | 12.20 | 28.10 | 11.60 | 10.33 | 5.58 |
| ZnO | | | | | | | 0.10 | 0.10 | | |
| Amorphous | 75.10 | 86.80 | 70.60 | 76.50 | 73.10 | 82.00 | 67.05 | 83.50 | 64.40 | 79.80 |

TABLE 6

| Phase | 11 FA | 11 GP | 12 FA | 12 GP | 13 FA | 13 GP | 14 FA | 14 GP | 15 FA | 15 GP |
|---|---|---|---|---|---|---|---|---|---|---|
| Anhydrite | | | | | | | | | 0.90 | |
| Hematite | | | | | | | | | 2.40 | 1.60 |
| Lime | 2.10 | 0.10 | 1.10 | 0.10 | 1.10 | 0.10 | 0.80 | 0.10 | | |
| Magnetite | | | | | | | 0.10 | | 3.70 | 3.20 |
| Mullite | 17.90 | 15.70 | 22.70 | 18.80 | 30.10 | 21.40 | 22.00 | 17.70 | | |
| Spinel | | | | | | | | | 6.10 | 6.20 |
| Thermonatrite | | 3.70 | | 4.80 | | 3.10 | | 3.90 | | |
| Thernardite | | | | | | | | | | 3.70 |
| Quartz | 22.10 | 5.10 | 10.50 | 6.30 | 9.40 | 8.50 | 7.90 | 6.60 | 0.80 | 1.10 |
| Amorphous | 57.90 | 75.30 | 65.70 | 69.90 | 59.40 | 66.80 | 69.20 | 71.60 | 86.10 | 84.20 |

TABLE 7

| Phase | 16 FA | 16 GP | 17 FA | 17 GP | 18 FA | 18 GP | 19 FA | 19 GP | 20 FA | 20 GP |
|---|---|---|---|---|---|---|---|---|---|---|
| Albite | 2.10 | 2.80 | | | | | | | | |
| Anhydrite | 0.30 | 0.20 | 0.30 | | 1.00 | | 0.40 | 0.30 | 0.30 | |
| Cristoballite | 0.90 | | | | | | | | | |
| Gehlenite | | | | | 3.20 | 1.70 | | | | |
| Grossular | | | | | 0.40 | 0.20 | | | | |
| Illmenite | | | | | 5.80 | 0.20 | | | | |
| Magnetite | 0.90 | 0.80 | | | 0.40 | 0.60 | 1.10 | 0.70 | 0.30 | 0.20 |
| Mullite | 7.60 | 4.00 | 1.50 | 1.00 | 0.60 | 0.40 | 4.80 | 3.80 | 2.30 | 1.70 |
| Periclase | | | 0.80 | 1.00 | 2.80 | 1.10 | | | | |
| Perovskite | | | 2.50 | 1.00 | 6.00 | 1.40 | | | | |
| Thermonatrite | | 3.90 | | | | | | 1.50 | | |
| Quartz | 5.30 | 3.70 | 9.00 | 4.60 | 5.60 | 3.10 | 20.90 | 13.40 | 12.20 | 7.90 |
| Amorphous | 82.90 | 84.60 | 85.90 | 92.20 | 74.20 | 91.30 | 72.80 | 79.90 | 84.90 | 90.20 |

TABLE 8

| Phase | 21 FA | 21 GP | 22 FA | 22 GP | 23 FA | 23 GP | 24 FA | 24 GP | 25 FA | 25 GP |
|---|---|---|---|---|---|---|---|---|---|---|
| Anhydrite | 2.10 | | 1.40 | | 2.30 | | 0.20 | 0.30 | | |
| Anorthite | 1.50 | | | | | | | | | |
| Diopside | | | | | | | | 2.30 | | |
| Gehlenite | 1.80 | 0.80 | 2.00 | 0.80 | 3.80 | 1.20 | | | 0.20 | 0.20 |
| Hematite | | | | | | | 0.50 | 0.30 | | |
| Hydrogarnet | | 9.30 | | 5.40 | | 1.00 | | | | |
| Jadeite | | 3.50 | 0.50 | 2.20 | 1.20 | 2.30 | | | | |
| Lime | 0.70 | | 0.50 | 0.40 | 0.40 | 0.10 | 0.10 | | 0.20 | 0.10 |
| Magnetite | | | | | | | | 0.30 | 0.40 | 0.40 |
| Mullite | | | | | | | 2.00 | 1.60 | 7.10 | 7.40 |
| Nosean | | 1.50 | | 1.20 | | 0.80 | | | | |
| Olympite | 1.30 | 2.30 | | 0.40 | | | | | | |
| Periclase | 1.20 | 0.70 | 1.20 | 0.60 | 2.00 | 0.90 | 0.20 | 0.40 | | |
| Perovskite | 9.10 | 0.80 | 5.10 | 1.50 | 6.30 | 2.40 | | | | |
| Quartz | 3.00 | 3.20 | 3.50 | 3.10 | 4.90 | 2.90 | 10.30 | 6.00 | 8.00 | 9.20 |
| Amorphous | 79.30 | 77.90 | 85.80 | 84.40 | 78.90 | 88.40 | 86.20 | 88.40 | 84.10 | 82.70 |

TABLE 9

| Phase | 26 FA | 26 GP | 27 FA | 27 GP | 28 FA | 28 GP | 29 FA | 29 GP | 30 FA | 30 GP |
|---|---|---|---|---|---|---|---|---|---|---|
| Albite | 0.60 | | 0.40 | | | | | | | |
| Anhydrite | | | 0.80 | | | | | | 0.40 | |
| Calcite | | | 0.20 | | | | | | | |
| Diopside | | 2.30 | 2.50 | 3.90 | | 0.50 | | | | |
| Gehlenite | | | | | | | | | | |
| Hematite | 1.20 | 0.40 | 2.40 | 2.00 | 0.30 | | | | 0.70 | 0.40 |
| Jadeite | | | | | | 5.50 | | | | |
| Lime | | | | | 0.80 | | | | 0.40 | |
| Magnesite | | | | | | | | | | |
| Magnetite | | | 4.30 | 3.60 | | | 2.70 | 2.90 | 2.50 | 2.40 |
| Mullite | 13.70 | 11.50 | 5.40 | 5.30 | 18.70 | 9.40 | 29.30 | 21.40 | 13.20 | 8.90 |
| Periclase | | | 0.40 | 0.30 | | | | | 0.40 | 0.40 |
| Thenardite | | | | 0.30 | | | | | | |
| Quartz | 15.40 | 9.70 | 5.20 | 3.90 | 7.70 | 3.50 | 10.00 | 6.00 | 11.70 | 6.70 |
| Amorphous | 69.10 | 76.10 | 78.40 | 80.70 | 72.50 | 81.10 | 58.00 | 69.70 | 70.00 | 81.20 |

TABLE 10

| Phase | 31 FA | 31 GP | 32 FA | 32 GP |
|---|---|---|---|---|
| Albite | | | 0.60 | |
| Calcite | 2.30 | | | |
| Diopside | | | | 2.30 |
| Hematite | | | 1.20 | 0.40 |
| Lime | 0.70 | | | |
| Magnetite | 0.90 | 0.80 | | |
| Mullite | 10.60 | 9.80 | 13.70 | 11.50 |
| Quartz | 12.40 | 9.80 | 15.40 | 9.70 |
| Amorphous | 73.10 | 79.60 | 69.10 | 76.10 |

Results displayed in Tables 4-10 show that crystalline phases remain after geopolymerization, but in smaller amounts than in the fly ash source material. The amount of the amorphous phase is higher in the geopolymer paste than in its precursor fly ash source material. The total amount of the amorphous phase in the fly ash source materials is closely related to the cooling rate of the fly ash after the combustion process. Slow cooling rates allow a higher degree of crystal formation, resulting in less amorphous phase in the fly ash material. The total amount of the amorphous phase affects geopolymerization since the amorphous phase is easier to dissolve by the alkaline activator solution, releasing more geopolymer precursor species, resulting in a higher degree of geopolymerization and higher compressive strength in the geopolymer concrete. The cooling rate of the fly ash source material may be controlled in the power plant at which the fly ash material is formed.

Table 11 shows the results of the measured mechanical properties of the geopolymer concrete samples. Concrete density, compressive strength, flexural strength, static elastic modulus, Poisson's ratio, and setting time were measured. Correlations were found between flexural strength and compressive strength, and between elastic modulus and compressive strength.

Fly ash source material samples having calcium oxide contents higher than 20% exhibited very rapid setting (e.g., less than three minutes). Thus, these fly ash source materials are not recommended for use as source materials of geopolymer concretes.

The density of the fresh geopolymer mixture was influenced mainly by the physical characteristics of the fly ash source material, such as specific gravity and particle size. The setting time of the geopolymer concrete was influenced mainly by the calcium oxide content in the fly ash source material. In order to reduce the number of dependent variables for analysis, only compressive strength values were used as responses. However, the flexural strength and elastic modulus can be obtained using the compressive strength value. The compressive strength of the geopolymer concrete was dependent upon a combination of physical, chemical, and crystallographic factors of the fly ash source material.

TABLE 11

| Fly Ash Type | Sample | Concrete Density (kg/m$^3$) | Compressive Strength (MPa) | Flexural Strength (MPa) | Elastic Modulus (MPa) | Poisson's Ratio | Setting Time (min) |
|---|---|---|---|---|---|---|---|
| C | 1 | 2323 | 59.50 | 4.48 | 33633 | 0.12 | 1.5 |
| C | 2 | 2323 | 52.28 | 4.72 | 34377 | 0.12 | 2 |
| C | 3 | 2291 | 55.89 | 4.30 | 37108 | 0.17 | 25 |
| F | 4 | 2307 | 40.35 | 4.14 | 28599 | 0.14 | 180 |
| F | 5 | 2291 | 47.55 | 5.58 | 29475 | 0.16 | 350 |
| F | 6 | 2307 | 46.69 | 5.30 | 29358 | 0.14 | 320 |
| F | 7 | 2307 | 46.79 | 4.61 | 28517 | 0.13 | 240 |
| F | 8 | 2291 | 46.11 | 4.71 | 26455 | 0.12 | 400 |
| C | 9 | 2339 | 80.37 | 5.27 | 42878 | 0.13 | 20 |
| F | 10 | 2243 | 47.44 | 5.12 | 25635 | 0.14 | 480 |
| F | 11 | 1986 | 12.20 | 2.24 | 7040 | 0.17 | 140 |
| F | 12 | 1970 | 12.82 | 2.38 | 6812 | 0.10 | 60 |
| F | 13 | 1986 | 20.68 | 3.50 | 7960 | 0.08 | 70 |
| F | 14 | 1890 | 10.34 | 2.74 | 7460 | 0.10 | 25 |
| F | 15 | 2371 | 46.56 | 6.31 | 28744 | 0.15 | 480 |
| F | 16 | 1810 | 5.53 | 1.15 | 4619 | 0.12 | 25 |
| C | 17 | 2307 | 61.38 | 6.23 | 31447 | 0.18 | 8 |
| C | 18 | 2323 | 39.19 | 4.19 | 19064 | 0.22 | 6 |
| F | 19 | 2291 | 43.38 | 4.24 | 25607 | 0.13 | 45 |
| C | 20 | 2371 | 53.70 | 4.43 | 28910 | 0.15 | 285 |
| C | 21 | 2323 | 36.54 | 3.58 | 26972 | 0.13 | 4 |
| C | 22 | 2323 | 57.18 | 5.27 | 29448 | 0.19 | 2 |
| C | 23 | 2339 | 42.81 | 5.18 | 22567 | 0.22 | 3 |
| C | 24 | 2355 | 64.68 | 4.90 | 30806 | 0.15 | 18 |
| C | 25 | 2355 | 62.19 | 4.83 | 29896 | 0.14 | 55 |
| F | 26 | 1938 | 20.16 | 2.79 | 11273 | 0.14 | 16 |
| F | 27 | 2339 | 52.57 | 4.17 | 28089 | 0.14 | 20 |
| F | 28 | 2083 | 32.45 | 4.38 | 22808 | 0.13 | 46 |
| F | 29 | 2195 | 23.36 | 2.52 | 13176 | 0.12 | 75 |
| F | 30 | 2131 | 22.68 | 3.94 | 12314 | 0.14 | 11 |
| C | 31 | 2163 | 36.24 | 3.25 | 21456 | 0.14 | 17 |
| F | 32 | 2243 | 36.80 | 4.56 | 24725 | 0.14 | 47 |
| F | 33 | 1906 | 49.24 | 4.66 | 19278 | 0.15 | 600 |
| C | 34 | 2211 | 2.73 | 0.62 | 1868 | 0.13 | 15 |
| F | MINIMUM | 1810 | 5.53 | 1.15 | 4619 | 0.08 | 11 |
| | MAXIMUM | 2371 | 52.57 | 6.31 | 29475 | 0.17 | 600 |
| | AVERAGE | 2144 | 33.19 | 3.95 | 19397 | 0.13 | 182 |
| C | MINIMUM | 2163 | 2.73 | 0.62 | 1868 | 0.12 | 1.5 |
| | MAXIMUM | 2371 | 80.37 | 6.23 | 42878 | 0.22 | 285 |
| | AVERAGE | 2310 | 50.33 | 4.38 | 27888 | 0.16 | 33 |

Compressive Strength:

Silica and alumina are the main precursors for the formation of the geopolymer network. Calcium oxide significantly influences the chemical structure of the geopolymer. However, the concentrations of silica, alumina, and calcium oxide in the fly ash source material cannot be used as predictors of the compressive strength of the geopolymer concrete without taking into consideration the crystalline arrangement of these species. Experiments showed that the crystalline part of the fly ash source material remained nearly inert while the amorphous phase was reactive throughout the geopolymerization reaction. Therefore, the amount of silica, alumina, and calcium oxide in a crystalline arrangement was not taken into account in the analysis; instead, it was assumed that only the silica, alumina, and calcium oxide in the amorphous phase participated in the geopolymerization reaction.

Each crystalline phase is composed of one or more elements in the form of oxides, e.g., Mullite is composed of 71.79% alumina and 28.21% silica. The chemical composition of each crystalline phase containing silica, alumina, and calcium oxide in the fly ash samples is shown in Table 12.

TABLE 12

| Crystalline phase | $SiO_2$ | $Al_2O_3$ | CaO | $Fe_2O_3$ |
|---|---|---|---|---|
| Albite | 67.39 | 20.35 | 1.07 | |
| Allophane | 34.7 | 45.29 | | |
| Anhydrite | | | 41.19 | |
| Anorthite | 44.4 | 35.84 | 19.2 | |
| Calcite | | | 56.03 | |
| Calcium Catena Silicate | 51.72 | | 48.28 | |
| Cristoballite | 100.00 | | | |
| Dicalcium Silicate | 31.5 | 2.1 | 63.5 | 0.9 |
| Diopside | 55.49 | | 25.9 | |
| Dolomite | | | 30.41 | |
| Gehlenite | 21.91 | 37.18 | 40.9 | |
| Grossular | 40.02 | 22.64 | 37.35 | |
| Gypsum | | | 32.57 | |
| Hematite | | | | 100 |
| Hydrogarnet | 21.75 | 24.61 | 40.6 | |
| Ilmenite | | | | 47.35 |
| Jadeite | 58.61 | 22.38 | | 3.89 |
| Lime | | | 100.00 | |
| Magnetite | | | | 100 |
| Merwinite | 36.56 | | 51.18 | |
| Mullite | 28.21 | 71.79 | | |
| Nosean | 35.61 | 30.21 | | |
| Perovskite | | | 41.25 | |
| Pseudobrookite | | | | 69.83 |
| Spinel | | 71.67 | | |
| Quartz | 100 | | | |

Using these values, the concentration of silica, alumina, and calcium oxide contained in the crystalline phases as shown by XRD analysis were subtracted from the total concentration of each species obtained by XRF analysis. To illustrate this process, the calculation of reactive silica concentration, reactive alumina concentration, and reactive calcium oxide concentration in sample one is explained. First, the crystalline phases containing silica, alumina, or calcium oxide present in the fly ash source material were identified from the data set forth in Tables 4-10. For sample one, the phases were Lime (0.30%), Merwinite (9.60%), and Quartz (23.10%). Then, the chemical composition of the crystalline phases was identified from the data set forth in Table 12. For sample one, Lime contains 100% calcium oxide, Merwinite contains 36.56% silica and 51.18% calcium oxide, and Quartz contains 100% silica. Next, the concentration of non-reactive silica, alumina, and calcium oxide was calculated using the following equation shown for the sample one calculation:

$$NRSiO_2 = \frac{C_{Quartz}*100 + C_{Merwinite}*36.56}{100} = \frac{23.10*100 + 9.60*36.56}{100} = 26.61\%$$

$$NRAl_2O_3 = 0$$

$$NRCaO = \frac{C_{Merwinite}*51.18 + C_{Lime}*100}{100} = \frac{9.60*51.18 + 0.30*100}{100} = 5.21\%$$

Finally, the non-reactive silica concentration, non-reactive alumina concentration, and non-reactive calcium oxide concentration are subtracted from the total concentrations (set forth in Table 2) to obtain the reactive silica concentration ($RSiO_2$), reactive alumina concentration ($RAl_2O_3$), and reactive calcium oxide concentration (RCaO). For sample one, the following calculation was performed:

$$RSiO_2 = SiO_2 - NRSiO_2 = 37.77 - 26.61 = 11.16\%$$

$$RAl_2O_3 = Al_2O_3 - NRAl_2O_3 = 19.13 - 0 = 19.13\%$$

$$RCaO = CaO - NRCaO = 22.45 - 5.21 = 17.24\%$$

Table 13 shows the values of reactive silica concentration, reactive alumina concentration, and reactive calcium oxide concentration for the fly ash source material samples. These values were used instead of the total concentration values obtained by XRF analysis to increase the accuracy of the model.

| Class | Sample | $RSiO_2$ | $RAl_2O_3$ | RCaO |
|---|---|---|---|---|
| C | 1 | 11.16 | 19.13 | 17.24 |
| C | 2 | 25.19 | 17.05 | 21.37 |
| C | 3 | 26.88 | 18.92 | 12.81 |
| F | 4 | 19.63 | 15.80 | 4.13 |
| F | 5 | 43.12 | 12.45 | 5.48 |
| F | 6 | 40.53 | 15.40 | 5.64 |
| F | 7 | 38.07 | 15.14 | 5.01 |
| F | 8 | 37.15 | 15.99 | 6.90 |
| C | 9 | 20.60 | 16.60 | 17.34 |
| F | 10 | 37.61 | 10.47 | 1.97 |
| F | 11 | 29.07 | 14.30 | 3.33 |
| F | 12 | 39.49 | 11.06 | 3.59 |
| F | 13 | 39.22 | 6.57 | 4.08 |
| F | 14 | 43.24 | 11.99 | 4.77 |
| F | 15 | 39.95 | 18.42 | 4.27 |
| F | 16 | 56.74 | 12.92 | 4.76 |
| C | 17 | 29.83 | 20.01 | 22.38 |
| C | 18 | 26.39 | 18.11 | 21.84 |
| F | 19 | 37.00 | 14.98 | 9.07 |
| C | 20 | 43.57 | 15.98 | 11.54 |
| C | 21 | 23.09 | 16.36 | 27.05 |
| C | 22 | 27.03 | 18.90 | 24.53 |
| C | 23 | 24.41 | 15.39 | 22.97 |
| C | 24 | 39.04 | 17.88 | 15.04 |
| C | 25 | 45.10 | 18.38 | 10.32 |
| F | 26 | 33.14 | 10.87 | 0.97 |
| F | 27 | 37.27 | 16.41 | 5.14 |
| F | 28 | 45.06 | 14.73 | 3.44 |
| F | 29 | 33.19 | 7.01 | 2.96 |
| F | 30 | 36.27 | 11.89 | 2.54 |
| C | 31 | 42.16 | 12.23 | 8.26 |
| F | 32 | 32.90 | 15.26 | 5.09 |

The values of reactive silica concentration, reactive alumina concentration, reactive calcium oxide concentration, LOI, mean particle size (d50), and specific surface area (SSA)

were used as regressors, while the compressive strength values were used as response. Three approaches were taken to develop a regression model. The models were developed using twenty-four samples, and validated with the remaining samples. First, the package LEAPS was used to perform subset selection, resulting in the following model:

$$f_C = -3.68 + 0.59*RSiO_2 + 3.35*RAl_2O_3 - 0.49*RCaO - 0.74*d50 - 4.40*LOI.$$

The LEAPS model had an adjusted $R^2$ value of 0.72 and an $R^2$ value of 0.78. The $R^2$ value had a 95% confidence interval of $0.66 \geq R^2 \geq 0.90$. The MSE was 75.18 and the variance inflation factor (VIF) values of the regressors were less than three; thus it was assumed there were no multicolinearity problems. The adequacy of the LEAPS model was analyzed through residual analysis.

Second, the package LARS was used for simultaneous subset selection and coefficient optimization using the LASSO algorithm, resulting in the following model:

$$f_C = -3.62 + 0.59*RSiO_2 + 3.35*RAl_2O_3 - 0.48*RCaO - 0.74*d50 - 4.39*LOI.$$

The LARS model had an adjusted $R^2$ value of 0.73 and an $R^2$ value of 0.78. The $R^2$ value had a 95% confidence interval of $0.66 \geq R^2 \geq 0.90$. The MSE was 75.18 and the VIF values were all below five. The adequacy of the LARS model was analyzed through residual analysis and with the remaining samples reserved for validation.

Third, the package GLMNET was used for subset selection and coefficient optimization using the EN algorithm, resulting in the following model:

$$f_C = 9.51 + 0.52*RSiO_2 + 2.16*RAl_2O_3 - 0.066*RCaO - 0.69*d50 - 1.70*LOI.$$

The GLMNET model had an adjusted $R^2$ value of 0.57 and an $R^2$ value of 0.65. The $R^2$ value had a 95% confidence interval of $0.48 \geq R^2 \geq 0.82$. The MSE was 89.73 and the VIF values were less than three indicating no signs of multicolinearity. The adequacy of the GLMNET model was analyzed through residual analysis and with the remaining samples reserved for validation.

Of the three above models, the LARS model was selected as the most preferred. Also, an attempt also was made to develop a practical model using silica, alumina, and calcium oxide concentrations instead of the reactive concentrations. This practical model was an attempt to avoid the use of XRD analysis and simplify the process for geopolymer concrete practitioners. The following practical model was developed:

$$f_C = 16.22 + 1.33*SiO_2 - 0.78*Al_2O_3 + 0.71*CaO - 0.90*d50.$$

The practical model had an adjusted $R^2$ value of 0.63 and an $R^2$ value of 0.70. The $R^2$ value had a 95% confidence interval of $0.54 \geq R^2 \geq 0.86$. Two of the VIF values were between five and six, which is slightly higher than the recommended range of zero to five indicating that silica and calcium oxide concentrations may be moderately correlated. However, the VIF values fall within the accepted range of zero to ten proposed by some sources. The adequacy of the practical model was analyzed through residual analysis and with the remaining samples reserved for validation. The practical model showed low accuracy and poor sensitivity to changes in the characteristics of the fly ash source material.

The following preferred model was developed using multiple regression analysis:

$$f_C = -69 + 0.69RSiO_2 - 1.35RCaO + 1.31fn + 24SSA - 8.76LOI$$

where $f_C$ is the compressive strength of the geopolymer concrete in MPa, $RSiO_2$ is the reactive silica concentration in the fly ash source material in weight percent, $RCaO$ is the reactive calcium oxide concentration in the fly ash source material in weight percent, fn is the percentage of fly ash particles passing 45 μm, SSA is the specific surface area in $m^2/g$, and LOI is the percentage of loss on ignition. The reactive silica concentration is the concentration of silica in the fly ash source material that is not contained in a crystalline phase. The reactive calcium oxide concentration is the concentration of calcium oxide in the fly ash source material that is not contained in a crystalline phase. The residuals of the preferred model were thoroughly examined to ensure the adequacy of the model. The VIF values for each predictor were between zero and ten, revealing that there is no significant multicollinearity between the predictors used in the model.

All models set forth above, including the preferred model, were developed using the wet cast geopolymer mix design set forth in Table 1. The preferred model, however, was extrapolated to a dry cast geopolymer mix design by testing the dry cast geopolymer using the known fly ash source materials. Table 14 sets forth the dry cast geopolymer mix design. An 8M sodium hydroxide solution was used, with a sodium silicate to sodium hydroxide ratio of 1.5. The activator solution to fly ash ratio was 0.25, and the bulk volume of the coarse aggregate was 0.61. The fly ash specific gravity was 2.28.

TABLE 14

| Material | Quantity (kg/m³) |
| --- | --- |
| Fly Ash | 440 |
| Fine Aggregate | 967 |
| Coarse Aggregate | 976 |
| Sodium Hydroxide | 44 |
| Sodium Silicate | 66 |

Results showed that the dry cast geopolymer mix design generated a hardened geopolymer product with 40% less strength than the wet cast geopolymer product. Therefore, the following model expresses the relationship between characteristics of the fly ash source material and the compressive strength of its dry cast geopolymer:

$$f_C = 0.60(-69 + 0.69RSiO_2 - 1.35RCaO + 1.31fn + 24SSA - 8.76LOI).$$

This dry cast geopolymer model may be used by technicians to predict the compressive strength of a dry cast geopolymer concrete prepared with a fly ash source material, or to select a favorable fly ash source material that will yield a desired compressive strength in a dry cast geopolymer concrete.

Figure 3:
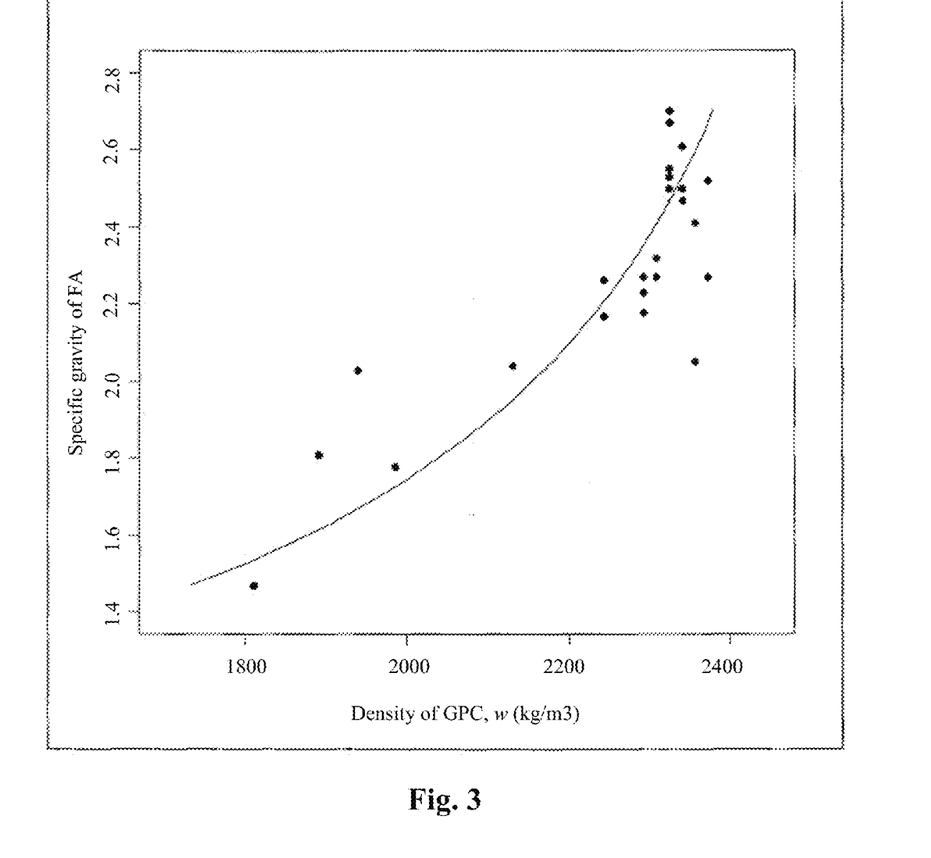
FIG. 3 is a graphical representation of the regression model relating the specific gravity of fly ash source materials to the density of geopolymer concretes.

Density:

The physical characteristics of the fly ash source materials were compared to the density of geopolymer concrete to identify possible correlations. Results showed that the specific gravity of the fly ash source material had the strongest correlation with the resulting geopolymer concrete density. The following regression model was obtained:

$$w = 2649 - 1979 \frac{1}{SG^2},$$

where w is the density of the geopolymer concrete as per ASTM standard C 138 and SG is the specific gravity of the fly ash source material determined following ASTM standard C 188. This regression model had an $R^2$ value of 0.76 with a 95% confidence interval of $0.61 \geq R^2 \geq 0.91$. FIG. 3 shows a scatter plot of the density of the geopolymer concrete versus the specific gravity of the fly ash source material along with a graphical representation of this regression model.

Figure 4:
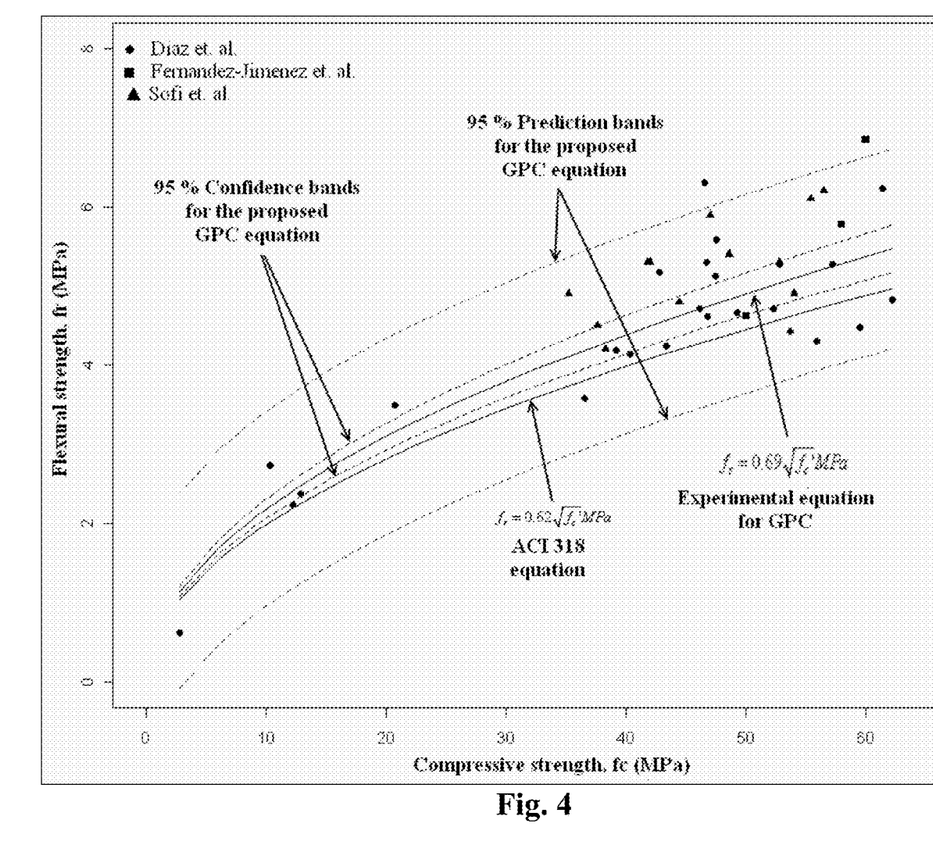
FIG. 4 is a graphical representation of the regression model relating the flexural strength of the geopolymer concrete to the compressive strength of the geopolymer concrete.

Flexural Strength:

FIG. 4 shows a scatter plot of the compressive versus the flexural strengths and a regression model representing the relationship between the two variables. The proposed regression model is:

$$f_r = 0.69\sqrt{f_C}$$

where $f_r$ is the flexural strength of the geopolymer concrete in MPa and $f_C$ is the compressive strength of the geopolymer concrete in MPa after three days of curing. The model accounts for 98.9% of the variability of the flexural strength and was obtained using the least squares technique. This model was found to best fit the experimental data after analyzing residuals and adjusted $R^2$ values of several different regression models. Shown in FIG. 4 are 95% confidence and prediction bands. FIG. 4 also shows mechanical strength data presented in Fernandez-Jimenez, A. M., Palomo, A., and Lopez-Hombrados C., *Engineering properties of alkali-activated fly ash concrete*, ACI Materials Journal, 103(2): 106-112 (2006), and mechanical strength data presented in Sofi, M., van Deventer, J. S. J., Mendis, P. A., and Lukey, G. C., *Engineering properties of inorganic polymer concretes (IPCs)*, Cement and Concrete Research, 37(2): 251-275 (2007). This experimental model for geopolymer concrete is similar to the equation given by ACI 318-08 section 8.5.2.3 to estimate the modulus of rupture for use in calculating deflections:

$$f_r = 0.62\sqrt{f_C}$$

where $f_r$ is the tensile flexural strength in MPa and $f_C$ is the compressive strength of OPC in MPa after 28 days of curing. The ACI equation is also shown in FIG. 4.

Figure 5:
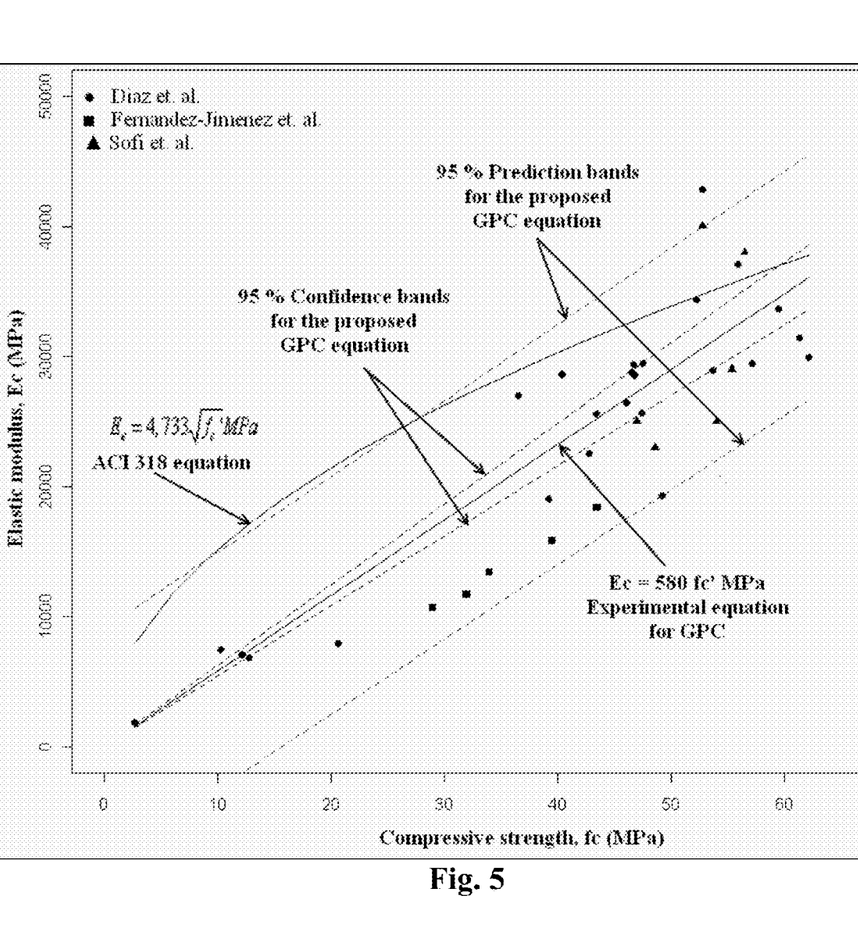
FIG. 5 is a graphical representation of the regression model relating the static elastic modulus of the geopolymer concrete to the compressive strength of the geopolymer concrete.

Static Elastic Modulus:

FIG. 5 shows a scatter plot of the compressive strength versus the static elastic modulus and a regression model representing the relationship between the two variables. The regression model obtained is:

$$E_C = 580 f_C$$

where $E_C$ is the static elastic modulus in MPa and $f_C$ is the compressive strength of the geopolymer concrete in MPa. This model captures 98.3% of the elastic modulus variability. FIG. 5 also includes the 95% confidence and prediction bands for the proposed regression model. For comparison, FIG. 5 shows mechanical strength data presented in Fernandez-Jimenez, 2006 and Sofi, 2007 (both cited above). A plot of the following equation presented in ACI 318-08 section 8.5.1 for computing the modulus of elasticity for normal weight concrete is also shown in FIG. 5:

$$E_C = 4,733\sqrt{f_C}$$

where $E_C$ is the static elastic modulus in MPa and $f_C$ is the compressive strength of the OPC in MPa.

Figure 6:
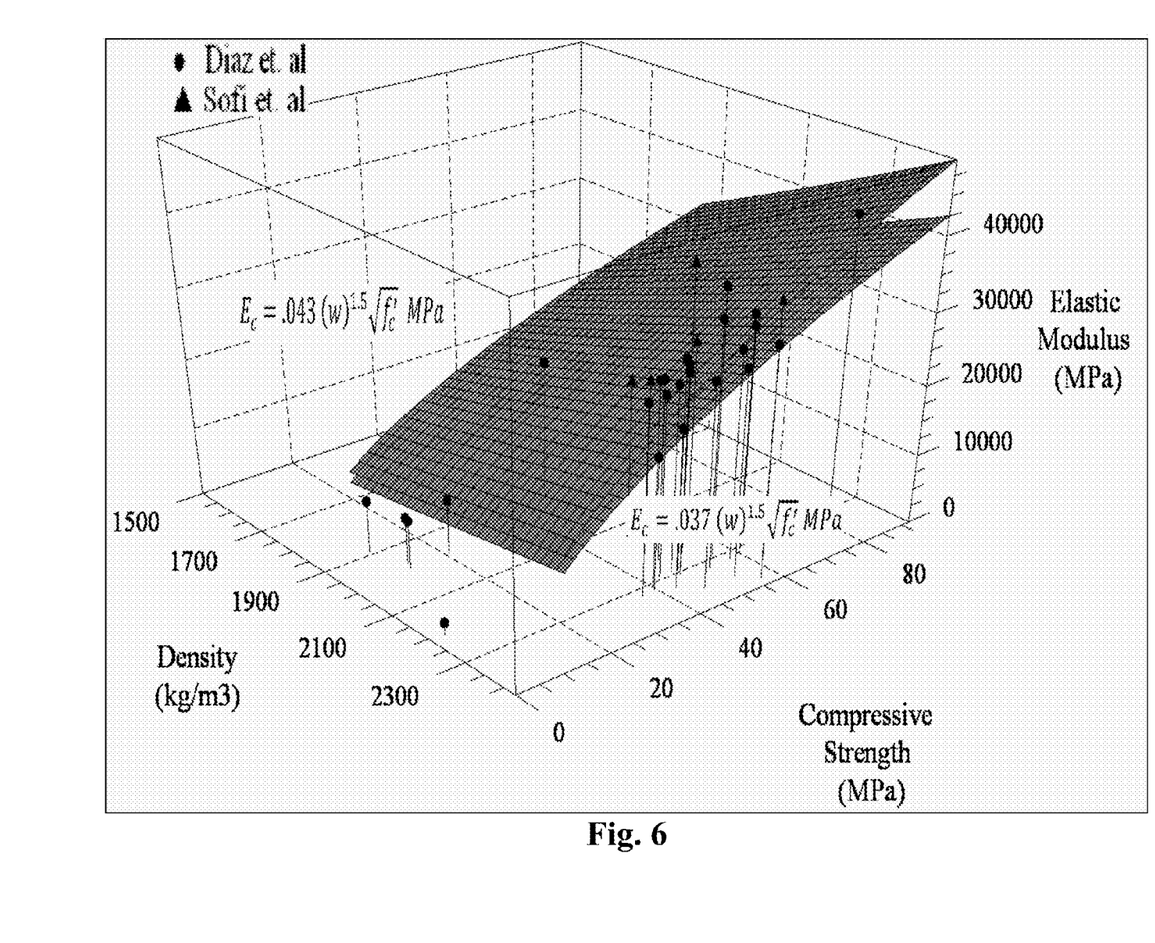
FIG. 6 is a graphical representation of the regression model relating the static elastic modulus of the geopolymer concrete to the compressive strength and density of the geopolymer concrete.

A second regression model was derived using the interaction between compressive strength and density of the geopolymer concrete as indicators of the elastic modulus:

$$E_C = 0.037(w)^{1.5}\sqrt{f_C}$$

where $E_C$ is the static elastic modulus in MPa, w is the density of geopolymer concrete in kg/m³, and $f_C$ is the compressive strength of the geopolymer concrete in MPa. Alternatively, if density in lb/ft³ is used for w, compressive strength in psi may be used for $f_C$. This model has an $R^2$ value of 98%, suggesting that the inclusion of density in the prediction model helps in capturing the variability in the elastic modulus of fly-ash-based geopolymer concretes. FIG. 6 shows this regression model, along with mechanical strength data presented in Sofi, 2007 (cited above). FIG. 6 also shows a plot of a similar equation given in ACI 318-08 section 8.5.1, which was derived from short-term tests of OPC ranging in density from 1,442 to 2,483 kg/m³ (or 90 to 155 lb/ft³):

$$E_C = 0.043(w)^{1.5}\sqrt{f_C}.$$

The statistically derived equations presented herein may be used to prepare dry cast geopolymer concrete from a fly ash source material and obtain consistent and predictable mechanical properties of the dry cast geopolymer concrete. Dry cast geopolymer concrete has a higher compressive strength, higher strength-gain rate, and significantly higher corrosion resistance as compared to dry cast OPC-based concrete. Furthermore, using a geopolymer binder instead of OPC can significantly reduce greenhouse gas emissions. The dry cast geopolymer concrete may be used for any application in which conventional dry cast concrete is used, such as hollow blocks, paving stones, panels, pipes, manholes, wet wells, diversion boxes, parking stoppers, light poles, utility boxes, retaining walls, traffic barriers, sound walls, or decorative countertops. The dry cast geopolymer concrete may be especially suitable for locations where acidic conditions are the main source of deterioration of concrete.

The models set forth herein may be used to select a fly ash source material that will yield mechanical property values in the geopolymer concrete that are at least as high as desired mechanical property values. For example, a concrete having a certain flexural strength may be needed for a certain application. A fly ash source material may be selected by first identifying available fly ash materials, then performing chemical and crystallographic analyses on one or more of the fly ash materials. The analytical results may be used to calculate a predicted compressive strength of a geopolymer concrete formed with each of the fly ash materials as the source material using the following formula if a wet cast geopolymer concrete needed:

$$f_C = -69 + 0.69 RSiO_2 - 1.35 RCaO + 1.31 fn + 24 SSA - 8.76 LOI.$$

Alternatively, the LEAPS, LARS, GLMNET, or practical equations may be used to calculate a predicted compressive strength of each hypothetical geopolymer concrete. If a dry cast geopolymer concrete is needed, the following formula may be used:

$$f_C = 0.60(-69 + 0.69 RSiO_2 - 1.35 RCaO + 1.31 fn + 24 SSA - 8.76 LOI).$$

From the calculated predicted compressive strength value, a predicted flexural strength may be calculated for each hypothetical geopolymer concrete formed with a fly ash material using the following formula:

$$f_r=0.69\sqrt{f_C}.$$

A fly ash source material may be selected by comparing the predicted flexural strength values to the required flexural strength of the specific application, and either (1) selecting the fly ash source material providing the highest predicted flexural strength, or (2) selecting a fly ash source material that provides a predicted flexural strength value that is equal to or greater than the required flexural strength. Then, a geopolymer concrete may be formed with the selected fly ash source material by mixing the following components: about 14 to about 24% by volume fly ash source material, about 25 to about 40% by volume fine aggregate, about 32 to about 41% by volume coarse aggregate, and about 1 to about 20% by volume alkaline activator solution.

While preferred embodiments of the present invention have been described, it is to be understood that the embodiments are illustrative only and that the scope of the invention is to be accorded a full range of equivalents, many variations and modifications naturally occurring to those skilled in the art from a review hereof

The invention claimed is:

1. A method of selecting a fly ash source material for a geopolymer concrete from a plurality of fly ash samples, the method comprising the steps of:
   a) setting a target compressive strength for the geopolymer concrete;
   b) measuring a set of properties of each of the plurality of fly ash samples, wherein the set of properties includes reactive silica concentration, reactive calcium oxide concentration, percentage of particles passing 45 μm, specific surface area, and loss on ignition;
   c) determining calculated values of the compressive strength for a geopolymer concrete formed with each of the plurality of fly ash samples using an equation relating the set of properties of the plurality of fly ash samples to calculated values of the compressive strength of the geopolymer concrete formed with each of the plurality of fly ash samples, wherein the equation comprises:

$f_C=-69+0.69RSiO_2-1.35RCaO+1.31fn+24SSA-8.76LOI$ or $f_C=0.60(-69+0.69RSiO_2-1.35RCaO+1.31fn+24SSA-8.76LOI)$, and wherein $f_C$ is the compressive strength of the geopolymer concrete in MPa, $RSiO_2$ is the reactive silica concentration in weight percent, RCaO is the reactive calcium oxide concentration in weight percent, fn is the percentage of fly ash particles passing 45 μm, and LOI is the percentage of loss on ignition;
   d) comparing the calculated values of the compressive strength of the geopolymer concrete formed with each of the plurality of fly ash samples with the target compressive strength;
   e) selecting one of the plurality of fly ash samples as the fly ash source material for the geopolymer concrete, wherein the fly ash source material yields a calculated value of the compressive strength that is equal to or greater than the target compressive strength; and
   f) preparing the geopolymer concrete with the fly ash source material.

2. The method of claim 1, wherein the equation comprises:

$f_C=-69+0.69RSiO_2-1.35RCaO+1.31fn+24SSA-8.76LOI.$

3. The method of claim 1, wherein the geopolymer concrete is a dry cast geopolymer concrete; and wherein the equation comprises:

$f_C=0.60(-69+0.69RSiO_2-1.35RCaO+1.31fn+24SSA-8.76LOI).$

4. The method of claim 1, further comprising the steps of:
   a1) setting a target value for a second mechanical property of the geopolymer concrete;
   c1) determining calculated values of the second mechanical property for the geopolymer concretes formed with each of the plurality of fly ash samples using a second equation relating calculated values of the compressive strength to calculated values of the second mechanical property; and
   d1) comparing the calculated values of the second mechanical property with the target value for the second mechanical property;
   wherein the fly ash source material yields a calculated value of the compressive strength that is equal to or greater than the target compressive strength and a calculated value of the second mechanical property that is equal to or greater than the target value for the second mechanical property.

5. The method of claim 4, wherein the second mechanical property comprises flexural strength; and wherein the second equation comprises:

$f_r=0.69\sqrt{f_C},$ wherein $f_r$ is the flexural strength of the geopolymer concrete in MPa and $f_C$ is the compressive strength of the geopolymer concrete in MPa.

6. The method of claim 4, wherein the the second mechanical property comprises static elastic modulus; and wherein the second equation comprises:

$E_C=580f_C,$ wherein $E_C$ is the static elastic modulus in MPa and $f_C$ is the compressive strength of the geopolymer concrete in MPa.

7. The method of claim 4, wherein the second mechanical property comprises static elastic modulus; and wherein the second equation comprises:

$E_C=0.037(w)^{1.5}\sqrt{f_C},$ wherein $E_C$ is the static elastic modulus in MPa, w is the density of the geopolymer concrete in kg/m$^3$, and $f_C$ is the compressive strength of the geopolymer concrete in MPa.

* * * * *